United States Patent [19]
Wilmet et al.

[11] Patent Number: 5,714,653
[45] Date of Patent: Feb. 3, 1998

[54] PROCESS FOR THE PREPARATION OF DIFLUOROMETHANE

[75] Inventors: Vincent Wilmet, Wavre; Francine Janssens, Vilvoorde, both of Belgium

[73] Assignee: Solvay, Brussels, Belgium

[21] Appl. No.: 617,419

[22] Filed: Mar. 18, 1996

[30] Foreign Application Priority Data

Mar. 16, 1995 [FR] France ................... 95 03185

[51] Int. Cl.$^6$ ................................................. C07C 17/08
[52] U.S. Cl. ............................................. 570/166; 570/168
[58] Field of Search ................................. 570/166, 168

[56] References Cited

U.S. PATENT DOCUMENTS

| | | |
|---|---|---|
| 2,005,711 | 6/1935 | Daudt et al. . |
| 2,749,374 | 6/1956 | Ruh et al. ................... 570/170 |
| 2,749,375 | 6/1956 | Ruh et al. . |
| 3,904,701 | 9/1975 | Schultz et al. ............. 570/166 |
| 5,208,395 | 5/1993 | Elsheikh . |

FOREIGN PATENT DOCUMENTS

| | | |
|---|---|---|
| 0 522 639 | 1/1993 | European Pat. Off. . |
| 6211707 | 8/1994 | Japan ........................... 570/168 |

*Primary Examiner*—Alan Siegel
*Attorney, Agent, or Firm*—Spencer & Frank

[57] ABSTRACT

Difluoromethane is produced by reaction, in the liquid phase, between dichloromethane and hydrogen fluoride, in the presence of a titanium or tin halide.

10 Claims, No Drawings

PROCESS FOR THE PREPARATION OF DIFLUOROMETHANE

The present invention relates to a process for the preparation of difluoromethane by reaction between hydrogen fluoride and dichloromethane.

Difluoromethane is a synthetic compound containing carbon, fluorine and hydrogen atoms but no chlorine. In this respect, it may constitute a substitute for fully halogenated chlorofluorohydrocarbons (CFCs), which are suspected of having a damaging effect on the ozone layer. This compound may prove to be particularly advantageous, alone or as a mixture, in certain applications in refrigeration and in air conditioning.

It has been known for a long time that difluoromethane may be prepared by hydrofluorination of dichloromethane in the liquid phase, in the presence of pentavalent antimony halides (patents U.S. Pat. No. 2,005,711 and U.S. Pat. No. 2,749,375). The antimony halide used in these known processes is, however, gradually converted into trivalent antimony halide, which is inactive as a catalyst for the reaction between dichloromethane and hydrogen fluoride and is particularly corrosive with respect to metal equipment.

It is moreover known, from patent U.S. Pat. No. 5,208,395, to prepare difluoromethane by reaction of dichloromethane with hydrogen fluoride in the gas-phase, in the presence of a catalyst consisting of tin tetrachloride deposited on active charcoal. The productivity of such a gas-phase process, per unit volume of the reactor, is, however, very low. In addition, this known process has a risk of deactivating the catalyst.

The aim of the present invention is to provide a process for the preparation of difluoromethane by reaction between hydrogen fluoride and dichloromethane and which process no longer has the drawbacks of the processes mentioned above.

The invention consequently relates to a process for the preparation of difluoromethane by reaction, in the liquid phase, of dichloromethane with hydrogen fluoride, according to which the reaction is performed in the presence of a catalyst comprising a halide of a metal chosen from titanium and tin.

The expression halide of a metal chosen from titanium and tin is understood to denote one or more titanium or tin salts formed from one or more halides, such as a titanium halide, a tin halide, a mixture of these halides or a mixed titanium and tin halide.

The catalyst preferably comprises at least 50% by weight of halide of a metal chosen from titanium and tin. Even more preferably, the catalyst consists essentially of halide of a metal chosen from titanium and tin.

A chloride or a fluoride is advantageously selected as halide. The use of a chloride is advantageous inasmuch as this compound is economical and readily available. A tetrachloride is preferably chosen. The use of a fluoride or of a chlorofluoride also gives good results. The latter compounds may be obtained from a chloride which is subjected to at least partial fluorination. This fluorination may be performed, for example, using hydrogen fluoride, prior to placing the catalyst in contact with dichloromethane. As a variant, it may be performed in situ, during the reaction of dichloromethane with the hydrogen fluoride.

Catalysts comprising a tin halide are preferred, mainly on account of their good activity in the process according to the invention when the latter is carried out continuously. Very good results have been obtained with tin tetrachloride as catalyst.

In the process according to the invention, the catalyst may be used in variable amounts. It is generally used in an amount of at least about 0.001 mol of catalyst per mole of dichloromethane. It is preferably used in an amount of at least 0.01 mol per mole of dichloromethane. Very good results have been obtained in the presence of at least about 0.05 mol of catalyst per mole of dichloromethane. In principle, there is no upper limit to the amount of catalyst used. For example, in a process performed continuously, the molar ratio between the catalyst and the dichloromethane in the liquid phase may be up to 1,000. However, in practice, not more than about 5 mol of catalyst are generally used per mole of dichloromethane. Preferably, about 1 mol is not exceeded and, even more preferably, about 0.5 mol of catalyst per mole of dichloromethane is not exceeded.

The process according to the invention may be carried out in a continuous or batchwise manner. It is understood that the amount of catalyst used is expressed, in a batchwise process, relative to the initial amount of dichloromethane used and, in a continuous process, relative to the stationary amount of dichloromethane present in the liquid phase.

In the process according to the invention, the hydrogen fluoride and the dichloromethane are used in the liquid state, in variable molar ratios. Generally, at least about 2 mol of hydrogen fluoride are used per mole of dichloromethane. Preferably this ratio is at least about 4. Usually, about 30 mol of hydrogen fluoride per mole of dichloromethane is not exceeded, values not exceeding about 20 being especially recommended.

The process according to the invention may be performed within wide temperature and pressure ranges, in which the reactants are liquid. Generally, the process is performed at a temperature of at least about 75° C. A temperature of at least about 90° C. is preferred. A temperature of at least about 100° C. is particularly preferred. Usually, in particular as a function of the admissible pressure, this temperature does not exceed about 160° C., temperatures below or equal to about 140° C. being especially recommended. Generally, the process is performed at a pressure of at least about 2 bar. A pressure of at least about 5 bar is preferred. A pressure of at least about 10 bar is particularly preferred. Usually, this pressure does not exceed about 50 bar, pressures below or equal to about 30 bar being especially recommended. The process is preferably performed at a temperature and a pressure at which, in addition, the difluoromethane produced is gaseous.

The residence time of the reactants in the reactor must be sufficient to allow the reaction of dichloromethane with hydrogen fluoride to take place with an acceptable yield. This residence time may readily be determined as a function of the operating conditions selected. In practice, the residence time of the reactants in the reactor is generally at least about 10 minutes. It is preferably at least about 20 minutes. Usually, this residence time does not exceed about 6 hours, values of less than or equal to about 3 hours being especially recommended.

The process according to the invention may be carried out in any type of reactor or equipment which allows the conditions described to be combined and, in particular, which allows the pressure and the hydrogen fluoride to be resisted. Usually, the process according to the invention is performed in a reactor equipped with a device for drawing off a stream of gas, for example in a reactor over which is mounted a column and a reflux condenser. This device makes it possible, by suitably regulating, to withdraw the difluoromethane and the hydrogen chloride produced as a gaseous phase, while at the same time keeping the unconverted hydrogen fluoride and dichloromethane in the reactor, along with, where appropriate, the majority of the chlorofluoromethane which may be produced by partial fluorination of the dichloromethane.

In one specific embodiment of the process according to the invention, the reaction is performed in the presence of a halogenated hydrocarbon having a boiling point of at least 25° C. at atmospheric pressure (other than dichloromethane). Halogenated hydrocarbons which are suitable in this specific embodiment of the process are, in particular, perchloroethylene, trichloroethylene, 1,1,2,2-tetrachloroethane and 1,1,1,3,3-pentafluorobutane.

In this specific embodiment of the process according to the invention, the proportion, in the liquid phase, of the halogenated hydrocarbon having a boiling point of at least 25° C. is at least equal to 5% of the total weight of the liquid phase. Preferably, it is at least equal to 10% of the total weight of the liquid phase. In general, this proportion does not exceed 75% of the total weight of the liquid phase. Advantageously, it does not exceed 50% of the total weight of the liquid phase.

The examples below illustrate the invention in a non-limiting manner.

EXAMPLE 1

0.6 mol of dichloromethane, 12 mol of hydrogen fluoride and 0.06 mol of titanium tetrachloride were introduced into a 0.5 l autoclave made of Hastelloy B2 alloy, equipped with a paddle stirrer and over which was mounted a jacketed condenser. The autoclave was then immersed in a thermostatically-controlled bath, maintained at a temperature of 110° C., and the pressure was adjusted to 15 bar. The condenser was maintained at a temperature of 20° C. After reaction for 5 hours, 93% of the dichloromethane used was converted, of which 89% was converted into difluoromethane and 11% into chlorofluoromethane.

EXAMPLE 2

The test of Example 1 was repeated with tin tetrachloride in place of the titanium tetrachloride. After reaction for 5 hours, 50% of the dichloromethane used was converted, of which 81% was converted into difluoromethane and 19% into chlorofluoromethane.

EXAMPLE 3

0.20 mol of $SnCl_4$, 7.50 mol of HF and 1.17 mol of dichloromethane were introduced into the reactor described in Example 1. The reactor was heated to 115° C. under a pressure of 23.5 bar absolute and the condenser was maintained at a temperature of 45° C. The reactor was then continuously supplied with 6.4 g/h of dichloromethane and 3 g/h of HF.

A difluoromethane productivity of 3.9 g/h at the condenser outlet was observed. The reaction was continued for 30 hours without any decrease in productivity being observed.

EXAMPLE 4

0.57 mol of $SnCl_4$, 0.95 mol of 1,1,2,2-tetrachloroethane and 7.5 mol of HF were introduced into the reactor described in Example 1. The reactor was heated to 130° C. under a pressure of 23.5 bar absolute and the condenser was maintained at a temperature of 45° C. The reactor was then supplied continuously with 12 g/h of dichloromethane and 8 g/h of HF.

A difluoromethane productivity of 6.5 g/h was observed. The reaction was continued for 100 hours without any decrease in productivity being observed.

We claim:

1. A process for the preparation of difluoromethane by reaction, in the liquid phase, of dichloromethane with hydrogen fluoride, characterized in that the reaction is performed in the presence of a catalyst comprising a halide of a metal chosen from titanium and tin.

2. The process of claim 1, in which the catalyst consists essentially of halide of a metal chosen from titanium and tin.

3. The process of claim 1, in which the halide is a chloride.

4. The process of claim 1, in which the catalyst is tin tetrachloride.

5. The process of claim 1, in which the catalyst is used in an amount of about 0.001 to 5 mol per mole of dichloromethane.

6. The process of claim 1, in which from 2 to 30 mol of hydrogen fluoride are used per mole of dichloromethane.

7. The process of claim 1, in which the reaction is performed at a temperature of about 75° to 160° C.

8. The process of claim 1, in which the reaction is performed at a pressure of about 2 to 50 bar.

9. The process of claim 1, in which the difluoromethane and the hydrogen chloride produced are withdrawn as a gaseous phase.

10. The process of claim 1, in which the reaction is performed in the presence of a halogenated hydrocarbon having a boiling point of at least 25° C. at atmospheric pressure.

* * * * *